_(12)_ United States Patent
Tate

(10) Patent No.: US 10,078,954 B1
(45) Date of Patent: Sep. 18, 2018

(54) READING TRACKING SYSTEM

(71) Applicant: Culin Tate, Patomic, MD (US)

(72) Inventor: Culin Tate, Patomic, MD (US)

( * ) Notice: Subject to any disclaimer, the term of this patent is extended or adjusted under 35 U.S.C. 154(b) by 0 days.

(21) Appl. No.: 15/920,851

(22) Filed: Mar. 14, 2018

(51) Int. Cl.
| | |
|---|---|
| *G06F 3/01* | (2006.01) |
| *G08B 21/18* | (2006.01) |
| *G06K 9/00* | (2006.01) |
| *A61B 5/00* | (2006.01) |
| *A61B 5/021* | (2006.01) |

(52) U.S. Cl.
CPC ............ *G08B 21/18* (2013.01); *G06F 3/013* (2013.01); *G06F 3/014* (2013.01); *G06K 9/00335* (2013.01); *A61B 5/021* (2013.01); *A61B 5/681* (2013.01); *G06F 3/011* (2013.01); *G06K 9/00671* (2013.01)

(58) Field of Classification Search
CPC ..... G06K 9/00671; G06K 2009/00738; G06K 2009/01; G06K 9/00308; G06K 9/00335; G06K 9/00677; G06K 9/00268; G06F 1/163; G06F 1/013; G06F 3/013; G06F 3/014; G08B 21/18; A61B 2562/0219; A61B 5/021; A61B 5/1112; A61B 5/681
See application file for complete search history.

(56) References Cited

U.S. PATENT DOCUMENTS

| | | | |
|---|---|---|---|
| 6,873,314 B1 | 3/2005 | Campbell | |
| 7,429,108 B2 | 9/2008 | Rosenberg | |
| 9,256,285 B2 | 2/2016 | Leroy et al. | |
| 9,256,784 B1 | 2/2016 | Taylor et al. | |
| 9,317,115 B2 | 4/2016 | Gobert et al. | |
| 9,672,421 B2 | 6/2017 | Tsou et al. | |
| 2003/0210226 A1 | 11/2003 | Ho et al. | |
| 2013/0021373 A1* | 1/2013 | Vaught | G02B 27/017 345/633 |
| 2013/0054622 A1 | 2/2013 | Karmarker et al. | |
| 2014/0085218 A1 | 3/2014 | Lee | |

(Continued)

OTHER PUBLICATIONS

Oliver Amft et al., Making Regular Eyeglasses Smart, IEEE CS, Jul.-Sep. 2015.

(Continued)

*Primary Examiner* — Benyam Haile
(74) *Attorney, Agent, or Firm* — Mehrman Law Office; Michael J. Mehrman

(57) ABSTRACT

A reading tracking system specifically designed for children including a wrist-worn arm motion and heart rate sensor coupled to a parental monitoring system, a game-style application for the child's use, and a group application useful in a classroom setting. The user's heart rate and arm movements are monitored to detect reading-related behavior states, such as reading, fallen asleep, distracted, and awoke after haven falling asleep states, independent from precise eye gaze tracking. Heart rate monitoring detects a high heart rate that is inconsistent with reading, a moderate heart rate indicative of a sedentary awake state consistent with reading, and a low hart rate indicating that the user has fallen asleep. Arm movement monitoring detects a high arm activity state that is inconsistent with reading, a moderate arm movement state or gestures consistent with page turning while reading, and a low arm activity rate indicating that the user has fallen asleep.

20 Claims, 4 Drawing Sheets

(56) References Cited

U.S. PATENT DOCUMENTS

| | | |
|---|---|---|
| 2014/0223462 A1 | 8/2014 | Aimone et al. |
| 2014/0347265 A1 | 11/2014 | Aimone et al. |
| 2015/0099946 A1 | 4/2015 | Shain |
| 2017/0237899 A1* | 8/2017 | Wexler ............... H04N 5/23222 348/207.11 |

OTHER PUBLICATIONS

Marguerite McNeal, Wearable Tech Weaves Its Way Into Learning, Edgesurge.com, Nov. 17, 2016.
Kai Kunze, Real-life Activity Recognition—Focus on Recognizing Reading Activities, CBDAR 2013, LNCS 8357, pp. 179-185, 2014.
Paul Marks, Fitbit for the mind: Eye-tracker watches your reading, Technology News, Feb. 12, 2014.
Maja Stikic et al. Multi-Graph Based Semi-Supervised Learning for Activity Recognition, IEEE Xplore: Sep. 22, 2009.

* cited by examiner

READING TRACKING SYSTEM

TECHNICAL FIELD

The present invention relates to reading tracking systems and, more particularly, to a reading tracking system suitable for a child that includes a wrist-worn arm motion and heart rate sensor coupled to a parental monitoring system, a game-style application for the child's use, and a group application useful in a classroom setting.

BACKGROUND

Considerable research and development has gone into reading detection and tracking systems. These systems generally focus on precise "gaze tracking" of eye movements to detect word-by-word reading progress. Reading tracking systems have been developed for a range of purposes, such assessing the effectiveness of online advertisements, detecting learning disabilities, and assisting in foreign language learning. These systems typically utilize cameras positioned to clearly view eye movements along with sophisticated algorithms to detect word-by-word reading progress. Gaze tracking tracing systems have come down in price with certain systems developed for the mass consumer market. For example, the Swedish firm Tobii Technology has commercialized an inexpensive gaze tracking system designed for the general public that uses an infrared camera trained on the reader's cornea to track eyeball movements. The camera can be built into a computer display screen, a headset such as Google Glass eyeglasses, or clipped to the top of a computer screen or tablet.

Conventional gaze tracking systems are not well suited for use by children, who become easily distracted, often fall asleep while reading, and may use reading to intentionally help them fall asleep. Gaze tracking systems designed for adults generally lack features and incentives specifically designed to be effective for children. A child may fidget and shift positions in ways that interfere with the gaze tracking system. Body-worn camera systems can be sufficiently uncomfortable to interfere with the child falling sleep. There is, therefore, a continuing need for reading tracking systems designed to be effective for children.

SUMMARY

The present invention solves these problems in a reading tracking system and method specifically designed for use by children. The reading tracking system includes a wrist-worn device with a heart rate monitor and an arm movement monitor. A reading-related state detector determines reading-related behavior states of the person wearing the wrist-worn device based on the measured inputs. The reading-related behavior states including at least a reading state and a fallen asleep state. A timer determines durations of the reading-related behavior states. A notification generator communicates reading-related notifications based on the reading-related behavior states. The reading-related notifications include at least a reading state notification and a fallen asleep notification.

A reading monitoring station separate from the wrist-worn device receives or generates and displays the reading-related notifications. The reading-related behavior states may further include a distracted while reading state and an awoke during the night state. The reading tracking system may also include a camera providing head position monitoring or eye gaze monitoring inputs. The reading monitoring station may engage interactive communications with the person wearing the wrist-worn device through messages displayed or played by the wrist-worn device.

Additionally or alternatively, the reading tracking system may further include a separate child's application that receives data connoting the reading-related behavior states and presents associated reading-related information through a game-style interface. The wrist-worn device may also communicate reading-related information through a game-style interface. The reading tracking system may communicate data connoting the reading-related behavior states to a group reading tracking system that presents the user's reading-related information in combination with reading-related information for other persons of a reading group. The reading tracking system may also communicate data connoting the reading-related behavior states to a central database that combines the data with reading-related information for other persons.

The reading monitoring station may be a local reading monitoring station that communicates with the wrist-worn device over a direct wireless communication link. Additionally or alternatively, a remote reading monitoring station may communicate with the wrist-worn device over a network access point and a network communication link. In various embodiments, the reading-related behavior detector, timer, and notification generator may be located on the wrist-worn device or another system component.

It will be understood that additional techniques and structures for implementing particular embodiments of the invention and accomplishing the associated advantages will become apparent from the following detailed description of the embodiments and the appended drawings and claims.

DETAILED DESCRIPTION

Figure 1:
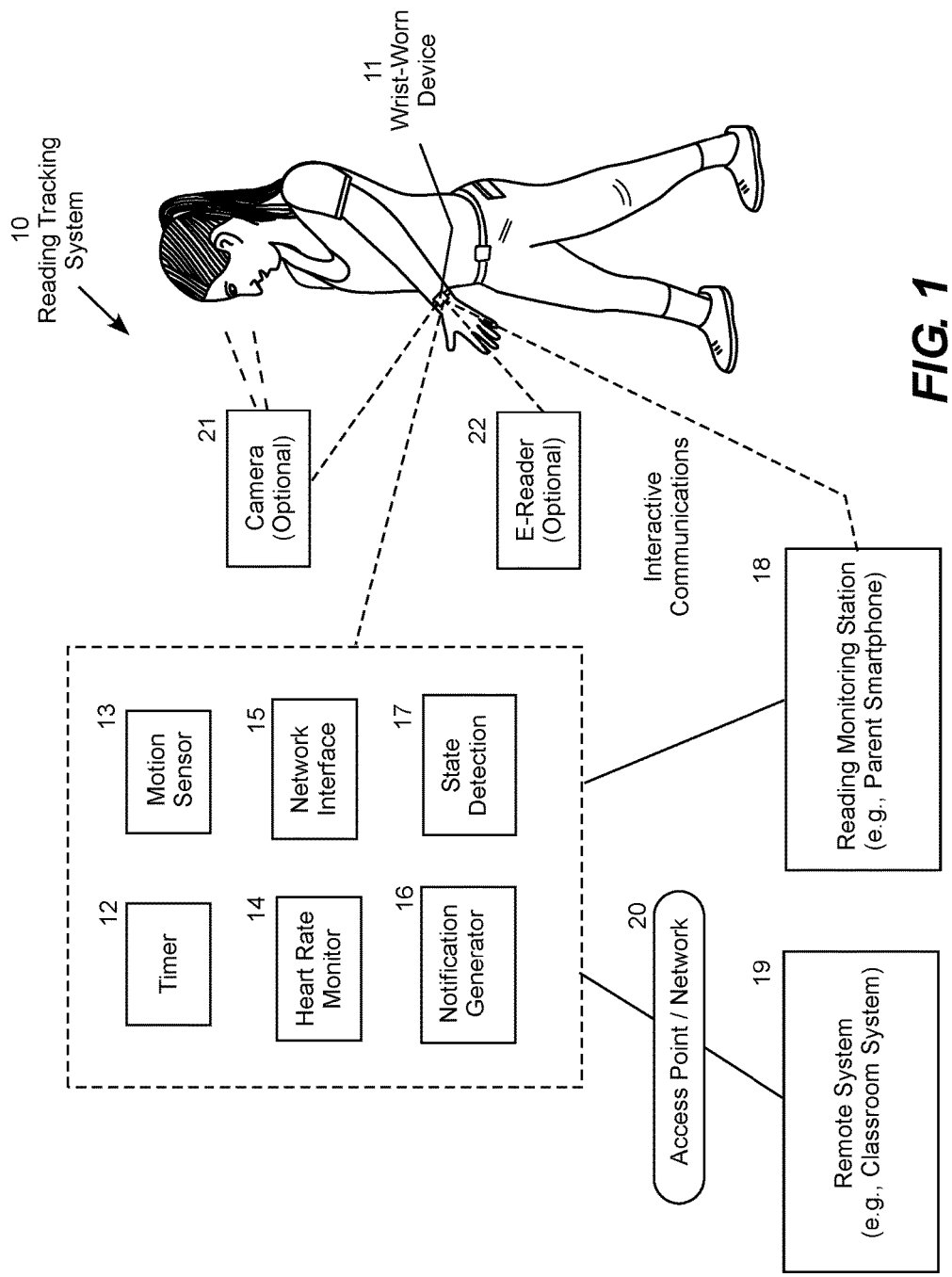
FIG. 1 is a functional block diagram of a reading tracking system specifically designed for use by a child.

This invention may be embodied in a reading tracking system specifically designed for use by children. The system includes a wrist-worn device that tracks the user's heart rate and arm movements to detect reading-related behavior states, such as reading, fallen asleep, distracted from reading, and awoke during the night states. For example, heart rate monitoring is used to determine a high heart rate that is inconsistent with reading, a moderate heart rate indicative of a sedentary awake state that is consistent with reading, and a low hart rate that indicates that the user has fallen asleep. The motion detector (e.g., accelerometer) detects arm movements including a high arm activity state that is inconsistent with reading, a moderate arm movement state or gestures consistent with page turning while reading, and a low arm activity rate that indicates that the user has fallen asleep. The reading-related behavior states may be determined independent from precise eye gaze tracking, although head movement or eye gaze tracking may be incorporated into the system if desired. As an option, the system may therefore include a camera that detects overly active head movement that is inconsistent with reading, an upright position with moderate head movement or gestures consistent with reading, and a slumped, inactive head position that indicates that the user has fallen asleep. A low-cost optical range camera may be used for head movement tracking. Camera data may also be used for eye gaze tracking, in which case an infrared camera may be used to track cornea movements.

The wrist-worn device typically communicates with a local reading monitoring station that monitors reading sessions, times reading sessions, tracks cumulative reading statistics, and provides real-time notifications (e.g., alarms) based on the parameters tracked by the wrist-worn device. Reading-related notification may include a notification when the child has completed a reading task (e.g., reading time, page turn count), when the child has fallen asleep, when the child has become distracted from reading, and when the child awakes after having fallen asleep when reading. For example, the local reading monitoring station may be deployed as an app running on a mobile phone maintaining with a Bluetooth or other wireless link with the wrist-worn device.

The reading monitoring station may also engage in interactive communications with the wrist-worn device, such as providing notifications to the reading monitoring station and receiving voice commands from the reading monitoring station. For example, a parent may use the reading monitoring station to receive a notification that the child has read for twenty minutes, and then send a message (e.g., voice, video, text, buzzer, etc.) to the child that it is time for lights out. As another example, the parent may also respond to a notification that the child has become distracted a using a message (e.g., voice, video, text, buzzer, etc.) communicated via the wrist-worn device.

To provide a few additional examples, a parent may use the reading monitoring station to convey over the monitoring device asking the child to "stop fooling around and get back to reading!"; "have you fallen asleep?" or "good job, time to turn out the lights now" and so forth. The child may respond using the monitoring device (e.g., wrist-worn device) with "ok Daddy" or "please tell Bobby to go to sleep." Interactive messages may be presented through voice or video communications played on the wrist-worn device and the remote monitoring station (e.g., smartphone).

The wrist-worn device (and/or the local reading monitoring station) may also communicate with the Internet via a wireless access point for integration with additional network or cloud-based systems. For example, the wrist-worn device may communicate with a group reading tracking system, such as a classroom system, that keeps track of reading assignments, reading time, and task completion for a class or other reading group. The wrist-worn device may also conduct network communications with a remote reading monitoring station that allows a parent or teacher, for example, to monitor the child's reading from a remote location. For instance, the remote reading monitoring station may provide a traveling parent, or a grandparent or mentor in a different location, with same of information, notification, and interactive communication features as the local reading monitoring station. The wrist-worn device may also communicate with the central database that aggregates data for individual and group analysis. For example, the central database may be used to conduct statistical analyses on large cohorts of reading profiles to conduct demographic reading analyses, conduct comparative reading analyses, rate reading progress against various peer groups, determine the effectiveness of the reading tracking system on reading behavior, detect reading disabilities, and so forth.

The wrist-worn device (and/or the local reading monitoring station) may also communicate with a child's application that runs on a separate computer with a larger display screen and better input devices, such as the child's tablet, smartphone, laptop or other computer. The child's application provides a game-style interface that presents the child's reading statistics in a fun and rewarding way. Illustrative techniques include game-like scoring for completion of reading tasks, electronic celebrations for completion of reading tasks and levels, allowing the child to earn various avatars associated with completion of reading tasks and levels, and so forth. The game interface can also interact with the group reading tracker to enable reading competitions among children in classes and other reading groups, such as local school classes and virtual classes that may include readers across the school district, the state or country. In this manner, reading can become a competitive or participation activity like sports, debate, robotics, spelling, and so forth. A variety of groups may sponsor and centrally administer reading competitions or participation programs, such as schools, governmental subdivisions, private clubs, church groups, universities, publishers, businesses, and so forth.

FIG. 1 is a functional block diagram of a reading tracking system 10 designed for use by a child. In an illustrative embodiment, the system includes a wrist-worn device 11 that includes a timer 12, a motion sensor 13 (e.g., accelerometer, MEMS gyroscope), a heart rate monitor 14, a network interface 15, and a notification generator 16. These measured inputs along with optional head position, gaze tracking, and/or e-reader page click measured inputs are provided to the state detection module 17. The input sensors each provide an indication of reading behavior in a range that varies in correlation with actual reading. The state detection module 17 determines relevant states, such as a "reading"; "fallen asleep"; "distracted from reading" and "awoke after having fallen asleep" states. State determination may be based on pattern matching using the measured data from the input sensors and reading patterns derived through research and observation, which can be updated from time to time based on the best research available. Feedback from the individual systems may also be used to calibrate the reading patterns based on observed behavior of individual readers. In combination, the input sensors and state detection module 17 provide a reliable indication of reading behavior without relying on precise gaze tracking, although precise gaze tracking may by included if desired.

To enable third-party (e.g., parental) monitoring, the wrist-worn device 11 maintains a communication link with a reading monitoring station 18. While any suitable direct or network communication link may be used, a direct wireless (e.g. Bluetooth) communication link is well suited for the connection. The reading monitoring station 18 typically engages in interactive communications with the wrist-worn device, such as providing notifications to the reading monitoring station and receiving voice and/or video commands from the reading monitoring station. The monitoring the wrist-worn device 11 may also maintain network communications with one or more online or cloud-based remote systems 19, such as a group reading tracking system, a remote parental monitoring system, a central database, and so forth. Network communications are typically facilitated by a local wireless access point 20, which may be a standalone network device or integrated into another network device, such as a router, gateway, hotspot, smartphone or the like. The e-reader 22 may be configured to provide interactive communications with the reading monitoring station and/or the remote system. For example, a parent using a local or remote reading monitoring station to monitor a child's reading may be able to communicate with the child using interactive voice and/or video via the e-reader 22 as an option or extension to similar capabilities provided by the wrist-worn device 11.

To enable head position and/or gaze tracking, the wrist-worn device 11 may be wirelessly linked to a camera 21, which is typically located in a computer screen (e.g., tablet, e-reader, laptop, smartphone or the like) or clipped on to a book or reading display device. The camera could also be mounted to a bedpost, lamp, window curtain, wall, ceiling, headgear, or any other suitable position in view of the child's reading position (e.g., the child's bed). As another option, the wrist-worn device 11 may be wirelessly linked to an e-reader 22 (e.g., Kindle, smartphone, tablet, etc.) which monitors and may alternatively or additionally include the camera 21 positioned for viewing the reader's head position and/or eye gaze movements.

Figure 2:
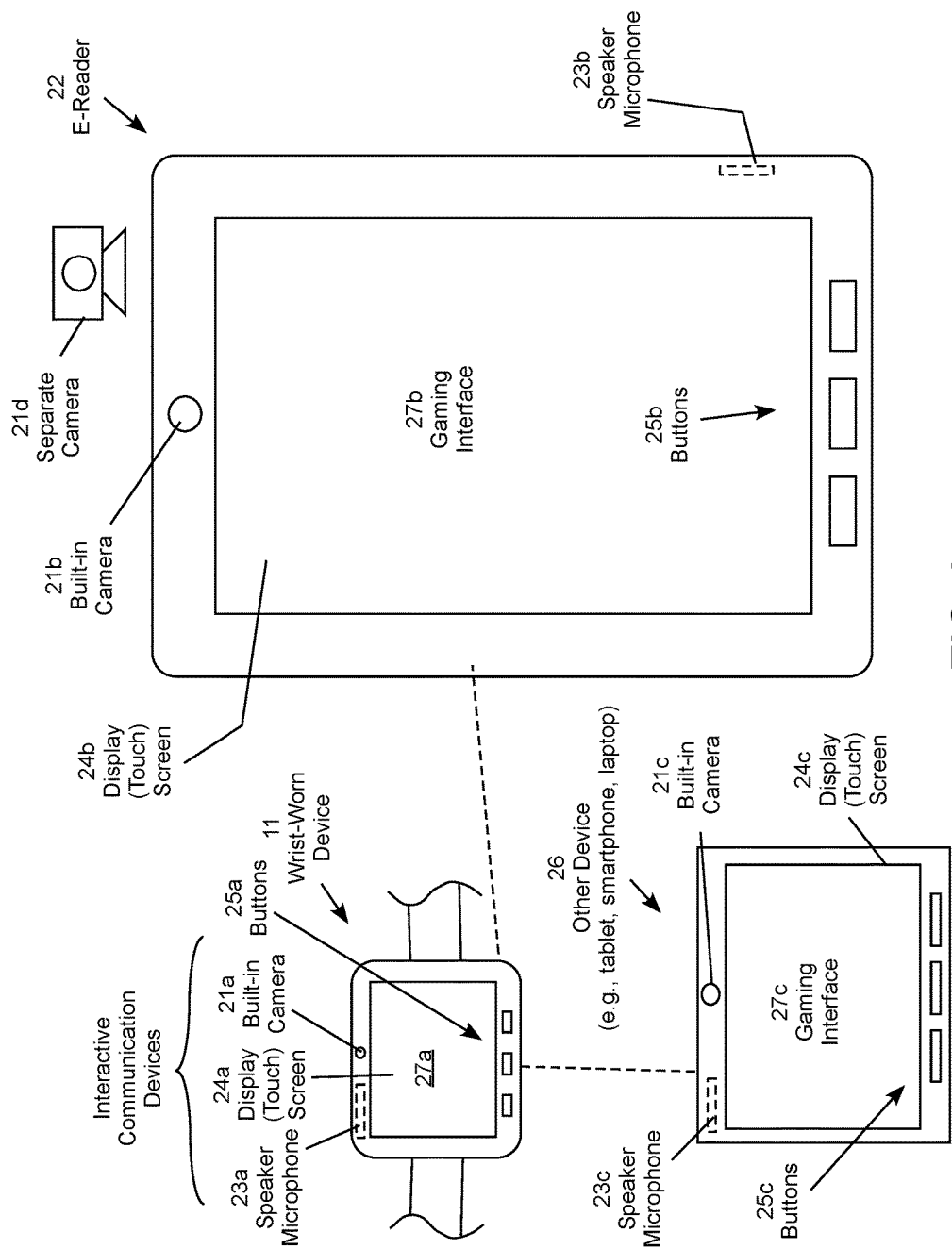
FIG. 2 is a conceptual illustration of components of the reading tracking system.

FIG. 2 is a conceptual illustration of components of the reading tracking system 10. The wrist-worn device 11 includes interactive communication features, such as a camera 21a, a speaker and microphone 23a, a display screen (e.g., touch screen) 24a, and buttons 25a. The e-reader 22 may likewise include interactive communication features including a camera 21b, speaker and microphone 23b, a display screen (e.g., touch screen) 24b, and buttons 25b. These interactive features may implement a gaming interface 27a to captivate the child's attention, reward reading accomplishments. These interactive features may also implement a gaming interface 27b to captivate the child's attention, reward reading accomplishments.

These same interactive features may be similarly implemented on any other electronic device that the child uses for reading, such as a smartphone, tablet, laptop computer. This feature it represented by the other device 26, which includes a camera 21c, a speaker and microphone 23c, a display screen (e.g., touch screen) 24c, and buttons 25c implementing a gaming interface 27c. The wrist-worn device 11 may also communicate with a separate camera 21d, such as a clip-on, free-standing or mounted camera. For example, the camera 21d may be clipped to a book or other paper reading material, or it may be mounted in a convenient position for viewing the child while reading. In addition to head position and/eye eye gaze tracking, the camera 21a-21d enable two-way video communications with the remote reading monitoring station 18.

Figure 3:
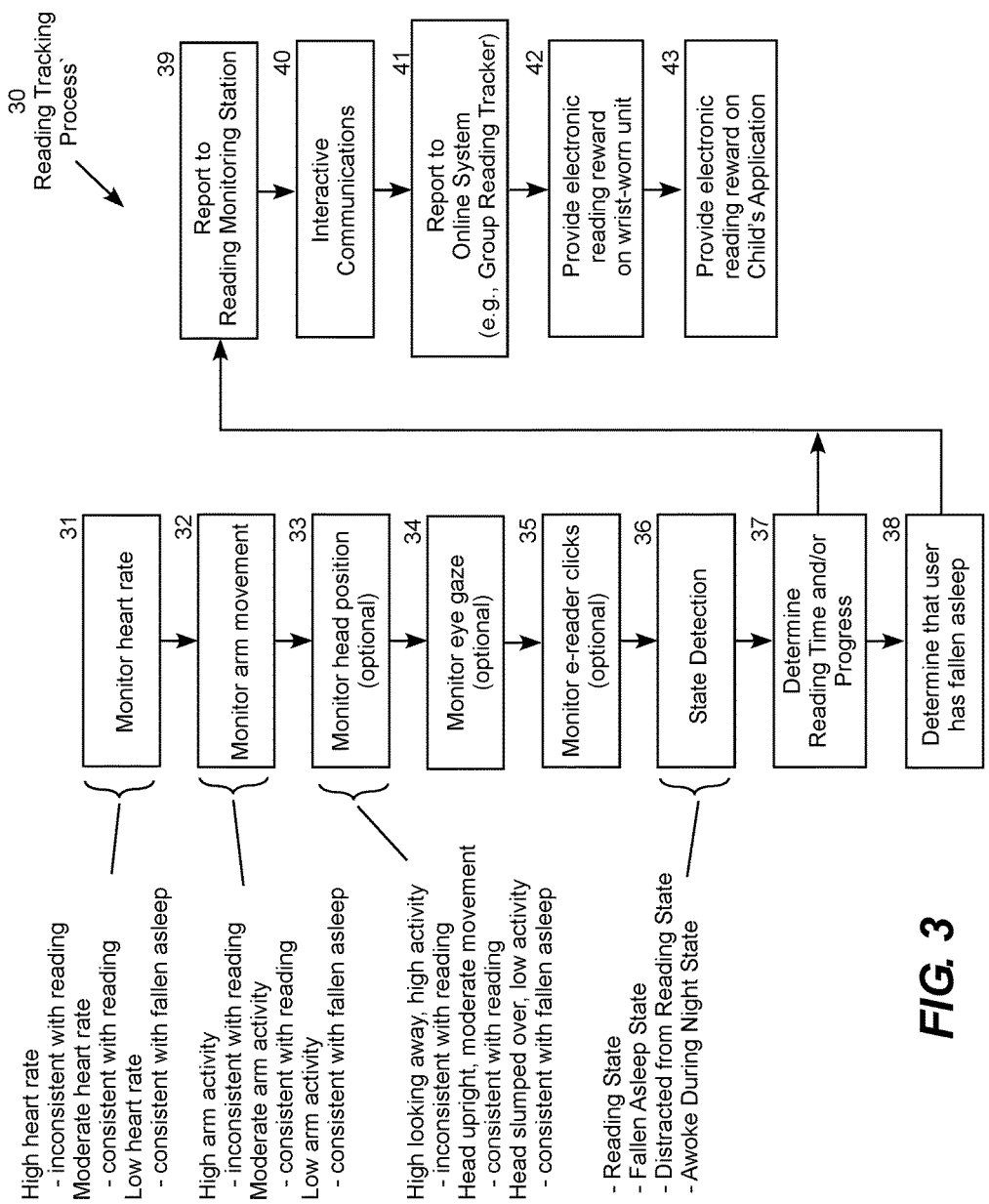
FIG. 3 is a logic flow diagram illustrating a process for operating the reading tracking system.

FIG. 3 is a logic flow diagram illustrating a process 30 for operating the reading tracking system 10. A portion of the process may be performed by an e-reader, camera or other computer device working in conjunction with the wrist-worn device 11. These devices will be referred to as the "monitoring device" for descriptive convenience. Some of the steps, such as those associated with head position or gaze tracking are optional. In step 31, the monitoring device monitors the child's heart rate. This generally includes at least (a) detecting a high heart rate that is inconsistent with reading, (b) detecting a moderate heart rate that is consistent with wakeful but sedentary activity consistent with reading, and (c) detecting a low heart rate that is consistent with the child having fallen asleep. Step 31 is followed step 32, in which the monitoring device monitors the child's arm movements. This generally includes at least (a) detecting high arm movement activity that is inconsistent with reading, (b) detecting moderate arm movement activity or gestures consistent with page turning or e-reader clicking indicative of reading, and (c) detecting low arm movement that is consistent with the child having fallen asleep.

Step 32 is followed step 33, in which the monitoring device monitors the child's head position. This generally includes at least (a) detecting the head looking away from a central position or moving in a manner that is inconsistent with reading, (b) detecting the head in an upright position moving moderately consistent with reading, and (c) detecting the head slumped with low activity consistent with the child having fallen asleep. Step 33 is followed step 34, in which the monitoring device monitors the child's eye gaze. Conventional techniques developed for eye gaze tracking known in the industry may be employed and will not be described further in this specification. Step 34 is followed step 35, in which the monitoring device receives page clicks from an associated e-reader. Step 35 is followed step 36, in which these inputs are used for reading state detection, which may range in sophistication from relatively simple (e.g., any of the monitored inputs indicating that the child is not reading) to sophisticated reading pattern matching techniques based on individual feedback and large group analysis.

Step 36 is followed step 37, in which the monitoring device determines reading time and/or progress. Step 37 is followed step 38, in which the monitoring device may determine that the child has fallen asleep. Step 37 and 38 are followed step 39, in which the monitoring device provides reading time and other notifications to one or more reading monitoring stations, which may include a local reading monitoring via a direct wireless communication link, and/or a remote reading monitoring station via a network communication link. Step 39 is followed step 40, in which the monitoring device and the reading monitoring station may engage in interactive communications.

Step 40 is followed step 41, in which the monitoring device and/or the reading monitoring station may engage in online communications to report reading data to one or more online systems, such as a group reading tracking system (e.g., classroom system), a remote reading monitoring station, a central database, and so forth. Step 41 is followed step 42, in which the monitoring device (e.g., the wrist-worn device, e-reader, or other reading device used at the time of reading) may display an electronic celebration in response to the child completing a reading task or attaining a reading level or goal. As another option, the monitoring device may determine that a preset time has elapsed or a reading increment has been completed, and then automatically provide positive feedback, instruct the child to go to sleep, and shut down. Step 42 is followed step 43, in which another related system, such as a child's application running on another computer, provides an electronic celebration when the child opens the reading tracker application on that device.

Figure 4:
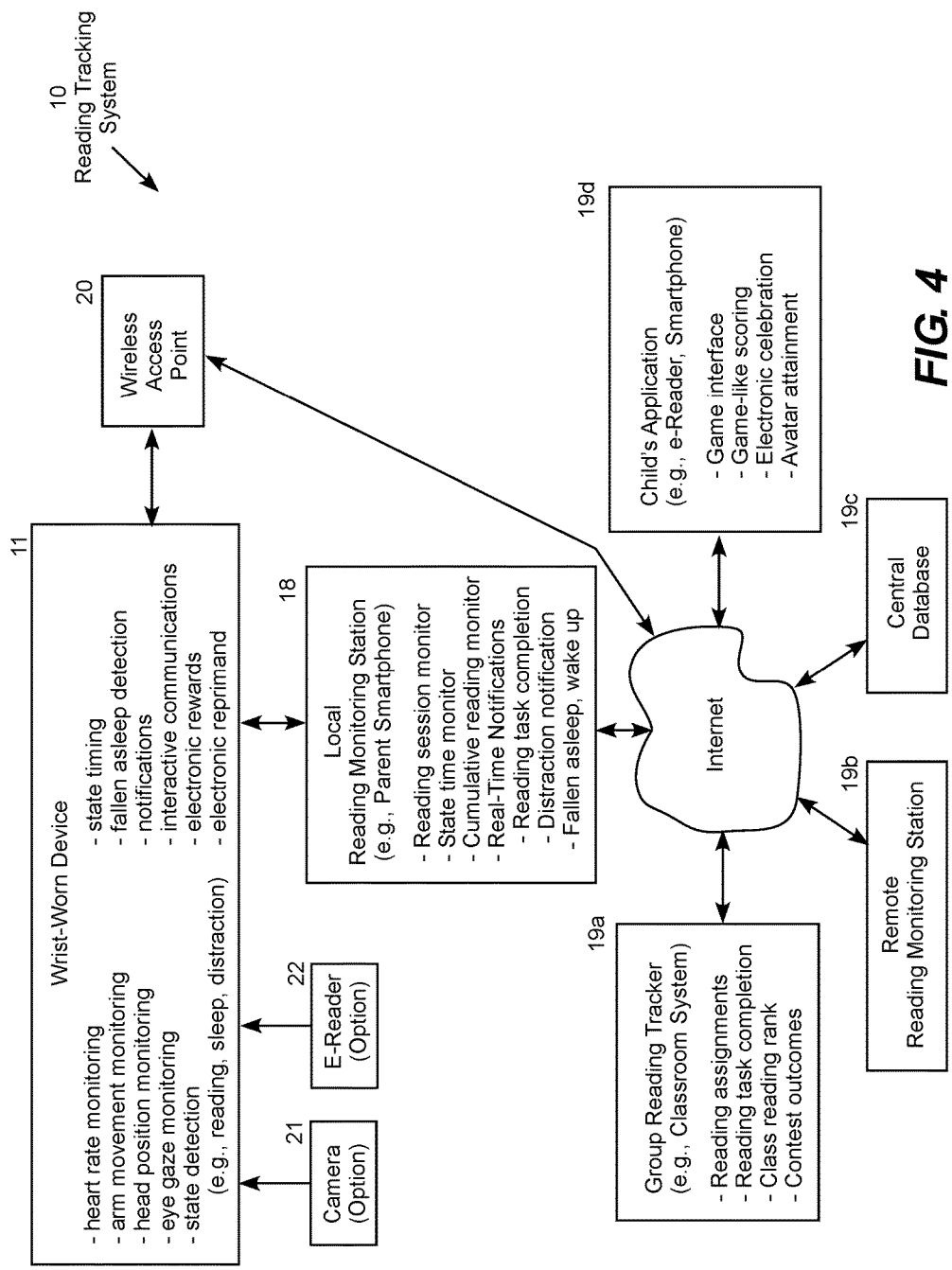
FIG. 4 is a functional block diagram illustrating network operations of the reading tracking system.

FIG. 4 is a functional block diagram illustrating network operations of the reading tracking system 10. The wrist-worn device 11 measures a variety of inputs used for reading detection without precise eye gaze tracking, including heart rate monitoring and arm movement monitoring. The wrist-worn device may receive additional inputs from an optional camera 21 viewing the child's head and/or eye movements, and an optional e-reader 22 tracking page-turning clicks. The camera 21 may also provide optional eye gaze tracking. The wrist-worn device detects reading behavior states of the child through suitable algorithmic techniques, such as applying thresholds to measured inputs, timing measured inputs, and pattern matching using multiple measured inputs. The wrist-worn device also times the detected states, such as reading, fallen asleep, and distracted-from-reading states.

The wrist-worn device also determines and communicates notifications (e.g., status, alarms, etc.) concerning detected states, such as "child is reading"; "child has been reading for a preselected time"; "reading task completed;" "reading time completed"; "child has fallen asleep;" "child has become distracted" and so forth. The wrist-worn device may also engage in interactive communications with other components, such as a local reading monitoring station 18. This may be a parental reading monitoring station running a reading monitoring app in the patent's smartphone. For example, the local reading monitoring station may communicate a voice or video message to the child through the wrist-worn device, such as "good job, time for lights out"; "have you fallen asleep?"; "cut it out and get back to reading" and so forth. The child may respond through the wrist-worn device with a voice or video (if a camera is utilized) message, for example saying "ok Daddy, good night" or another desired response. The wrist-worn device may also play electronic rewards and reprimands based on detected behavior. For example, the wrist-worn device may automatically play an electronic celebration when a reading task is completed, which may include a recorded positive feedback message in the parent's voice. On the other hand, the wrist-worn device may also automatically play an electronic reprimand when reading distraction is detected, which may include, for example, a buzzer, beep, or a recorded corrective feedback message in the parent's voice. Any suitable type of messages may be exchanged, such as voice, video, text, buzzer, etc. An advantage of this system is the ability to communicate messages through the voice or video of an authority figure, such as a parent, which a child may pay attention to. A user, such as the parent, may be able select the type of messages employed to allow age appropriate personalization of the system.

The wrist-worn device 11 typically communicates through local wireless links (e.g., Bluetooth) with nearby devices, such as the local reading monitoring station 18, a wireless access point 20, and the optional camera 21 and/or e-reader 22. The wireless access point 20, in turn, connects the wrist-worn device and/or the local reading monitoring station 18 with a variety of online or cloud-based resources, such as the group reading tracking system 19a, a remote reading tracking system 19b, a central database 19c, and a child's application 19d. The local reading monitoring station 18 monitors reading sessions and other states, such as fallen asleep and distraction. The local reading monitoring station also monitors cumulative reading progress, such as progress on a curriculum, reading statistics to gauge effectiveness of the reading monitoring program, distraction monitoring, reading disability detection, and sleep monitoring, which may include notifications and statistics reflecting when the child falls and when the child wakes up in the night. Analyses can then be conducted to determine the extent to which reading, the length time spent reading at night, the type of content read, the type of game interfaces utilized, the type of interactive communications, and other factors contribute to the child falling asleep as well as sleeping well through the night. The sleep monitoring, notification and statistical analysis feature is, in an of itself, and important benefit provided by the system.

The group reading tracking system 19a may be a classroom or other group system in which multiple participants (e.g., students) participate to complete coursework. The group reading tracking system may be used to implement competitive reading contests and peer-group rankings for multiple participants in the same reading group. Interactive communications between the group reading tracking system and the local reading monitoring station 18 and the child's application 19d may be used to communicate reading assignments, reading task completion status, group rankings, contest outcomes, and so forth.

The remote reading tracking system 19b typically provides an online equivalent to the local reading monitoring station 18 to allow remote monitoring and interactive communications with the writs worn device 11. For example, a parent may use the remote reading tracking system when traveling. As another option, a reading coach or other authorized person, such as a grandparent, may be authorized to interact with the child through the network link between the remote reading tracking and the wrist-worn device 11 and/or the child's application 19d.

The central database 19c provides a location for group or global storage of reading statistics. This allows reading analyses to be conducted, typically on an anonymous basis, on large populations for research and development purposes. To provide a few illustrative examples, studies may be conducted to determine the effectiveness of the reading tracking system on reading behavior, to detect population-wide occurrences of reading disabilities, to determine the effectiveness of the reading tracking system on reading behavior in children with ADHD, autism and other conditions.

The child's application 19d is typically implemented by an application running on another computer used by the child, such as a smartphone, tablet or laptop computer with a larger display screen and more extensive input devices than the wrist-worn device 11. The child's application typically presents reading tasks and completion information in a fun and engaging manner specifically designed to encourage and reward reading by children. Illustrative techniques include game-like scoring for completion of reading tasks, electronic celebrations for completion of reading tasks and levels, allowing the child to earn various rewards, such as avatars, tokens, digital rewards and so forth, associated with completion of reading tasks, achieving reading levels, and other accomplishments. The game interface can also interact with the group reading tracker to enable reading competitions among children in classes, such as local school classes and virtual classes that may include readers across the school district, the state or country. In this manner, reading can become a competitive or participation activity like sports, debate, robotics, spelling, and so forth. A variety of groups may sponsor reading competitions or participation programs, such as schools, governmental subdivisions, private clubs, church groups, universities, publishers, businesses, and so forth.

It should be appreciated that while the arm movement and heart rate sensors are located on the wrist-worn device, the timer function may be performed by the wrist-worn device, by the local reading monitoring station 18, the remote reading monitoring station 19b, or another system component as a matter of design choice. Similarly, the determination of reading-related states (e.g., reading state, fallen asleep state, distracted from reading state, an awoke after having fallen asleep state) may be determined by the wrist-worn device 11, the local reading monitoring station 18, by the remote reading monitoring station 19b, or another system component as a matter of design choice. The reading-related notifications based on the measured inputs may likewise be determined by the wrist-worn device 11, the local reading monitoring station 18, by the remote reading monitoring station 19b, or another system component as a matter of design choice.

It will be appreciated that the invention may be used for a wide range of reading tracking systems. The representative reading tracking example is provided as an illustrative embodiment without limiting the scope and applicability of the invention. The present disclosure is particularly well suited to implementation on portable computing devices, which may communicate with a server system providing access to a number of client systems over a network, or as a dedicated computing system. As such, embodiments of the disclosure may comprise adapting or reconfiguring presently existing equipment. Alternatively, original equipment may be provided embodying the disclosure.

All of the methods described in this disclosure may include storing results of one or more steps of the method embodiments in a non-transient storage medium. The results may include any of the results described in this disclosure and may be stored in any manner known in the art. The storage medium may include any storage medium described in this disclosure or any other suitable storage medium known in the art. After the results have been stored, the results can be accessed in the storage medium and used by any of the method or system embodiments described in this disclosure, formatted for display to a user, used by another software module, method, or system, etc. Furthermore, the results may be stored permanently, semi-permanently, temporarily, or for some period of time. For example, the storage medium may be random access memory (RAM), and the results may not necessarily persist indefinitely in the storage medium.

Those having skill in the art will appreciate that there are various vehicles by which processes and/or systems and/or other technologies described in this disclosure can be implemented (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described in this disclosure may be implemented, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that various implementations may employ any suitable type of hardware, software, and/or firmware.

Those skilled in the art will recognize that it is common within the art to describe devices and/or processes in the fashion set forth in this disclosure, and then use engineering practices to integrate such described devices and/or processes into data processing systems. That is, at least a portion of the devices and/or processes described can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems. All of the technology described in this disclosure is suitable for implementation using commercially available computing devices, such as network servers operated by the situational awareness system and smartphones or personal computers operated by members and customers. These computing devices may be interconnected via the Internet, mobile telephone voice and data system, or other data suitable network.

This disclosure sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components may be combined to achieve a particular functionality can be seen as "associated with" each other such that the desired functionality is achieved, irrespective of architectures or intermediate components. Likewise, any two components so associated can also be viewed as being "connected", or "coupled", to each other to achieve the desired functionality, and any two components capable of being so associated can also be viewed as being "functionally connected" to each other to achieve the desired functionality. Specific examples of functional connection include but are not limited to physical connections and/or physically interacting components and/or wirelessly communicating and/or wirelessly interacting components and/or logically interacting and/or logically interacting components.

While particular aspects of the present subject matter have been shown and described in detail, it will be apparent to those skilled in the art that, based upon the teachings of this disclosure, changes and modifications may be made without departing from the subject matter described in this disclosure and its broader aspects and, therefore, the appended claims are to encompass within their scope all such changes and modifications as are within the true spirit and scope of the subject matter described in this disclosure. Although particular embodiments of this disclosure have been illustrated, it is apparent that various modifications and embodiments of the disclosure may be made by those skilled in the art without departing from the scope and spirit of the disclosure. Accordingly, the scope of the disclosure should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. The disclosure is defined by the following claims, which should be construed to encompass one or more structures or function of one or more of the illustrative embodiments described above, equivalents and obvious variations.

The invention claimed is:

1. A reading tracking system, comprising:
   a wrist-worn device comprising a timer and sensors configured to measure inputs for a person wearing the wrist-worn device, the sensors including at least a heart rate monitor and an arm movement monitor;
   a reading-related state detector configured to determine reading-related behavior states of the person wearing the wrist-worn device based on the measured inputs from the heart rate monitor and the arm movement monitor, the reading-related behavior states including at least a reading state and a fallen asleep state;
   the timer configured to determine durations of the reading-related behavior states;
   a notification generator configured to communicate reading-related notifications based on the reading-related behavior states, the reading-related notifications including at least a reading state notification and a fallen asleep notification;
   a reading monitoring station separate from the wrist-worn device and in a different location from the location of the person wearing the wrist-worn device configured to receive or generate and display the reading-related notifications for monitoring the reading-related behavior states of the person wearing the wrist-worn device from the different location.

2. The reading tracking system of claim 1, wherein the reading-related behavior states further comprise a distracted while reading state.

3. The reading tracking system of claim 1, wherein the reading-related behavior states further comprise an awoke during the night state.

4. The reading tracking system of claim 1, further comprising a camera and wherein the measured inputs further comprise head position monitoring based on data provided by the camera.

5. The reading tracking system of claim 1, further comprising a camera and wherein the measured inputs further comprise eye gaze monitoring based on data provided by the camera.

6. The reading tracking system of claim 1, wherein the reading monitoring station is configured to engage interactive communications with the person wearing the wrist-worn device through messages displayed or played by the wrist-worn device.

7. The reading tracking system of claim 1, wherein the wrist-worn device is configured to communicate reading-related information through an interface comprising scoring for completion of reading tasks and electronic celebrations for completion of reading tasks and levels.

8. The reading tracking system of claim 1, further comprising a separate child's application configured to receive data connoting the reading-related behavior states and present associated reading-related information through an interface comprising scoring for completion of reading tasks and electronic celebrations for completion of reading tasks and levels.

9. The reading tracking system of claim 1, further comprising a group reading tracking system configured to receive data connoting the reading-related behavior states and present associated reading-related information in combination with reading-related information for other persons of a reading group.

10. The reading tracking system of claim 1, further comprising a central database configured to receive data connoting the reading-related behavior states along with reading-related information for other persons.

11. The reading tracking system of claim 1, wherein the reading monitoring station is a local reading monitoring station configured to communicate with the wrist-worn device over a direct wireless communication link.

12. The reading tracking system of claim 1, wherein the reading monitoring station is a remote reading monitoring station configured to communicate with the wrist-worn device over a network access point and a network communication link.

13. The reading tracking system of claim 1, wherein the wrist-worn device comprises the reading-related behavior detector.

14. The reading tracking system of claim 1, wherein the wrist-worn device comprises the timer.

15. The reading tracking system of claim 1, wherein the wrist-worn device comprises the notification generator.

16. A method for tracking reading, comprising:
   receiving measure inputs for a person wearing from a wrist-worn device worn by the person, the measured inputs including at least heart rate sensor data and an arm movement sensor monitor;
   determining reading-related behavior states of the person wearing the wrist-worn device based on the measured inputs from the heart rate monitor and the arm movement monitor, the reading-related behavior states including at least a reading state and a fallen asleep state;
   timing durations of the reading-related behavior states;
   generating and communicating reading-related notifications based on the reading-related behavior states, the reading-related notifications including at least a reading state notification and a fallen asleep notification to a different location from the location of the person wearing the wrist-worn device;
   displaying the reading-related notifications for monitoring the reading-related behavior states of the person wearing the wrist-worn device from the different location.

17. The method of claim 16, wherein the reading-related behavior states further comprise one or more of a distracted while reading state and an awoke during the night state.

18. The method of claim 16, further comprising receiving camera data and wherein the measured inputs further comprise one or more of a head position monitoring based on data provided by the camera and eye gaze monitoring based on data provided by the camera.

19. The method of claim 16, further comprising displaying reading-related data connoting the reading-related behavior states through an interface comprising scoring for completion of reading tasks and electronic celebrations for completion of reading tasks and levels.

20. The method of claim 16, further comprising conducting interactive communications related to the reading-related behavior states between the wrist-worn device worn and a separate reading monitoring station.

* * * * *